US008595499B2

(12) United States Patent
Haider et al.

(10) Patent No.: US 8,595,499 B2
(45) Date of Patent: Nov. 26, 2013

(54) METHOD FOR IDENTIFYING A PATIENT FOR LATER ACCESS TO AN ELECTRONIC PATIENT RECORD FOR THE PATIENT USING A COMMUNICATION DEVICE BELONGING TO AN INQUIRING PERSON

(75) Inventors: Sultan Haider, Erlangen (DE); Georg Heidenreich, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 945 days.

(21) Appl. No.: 11/755,143

(22) Filed: May 30, 2007

(65) Prior Publication Data

US 2007/0283156 A1   Dec. 6, 2007

(30) Foreign Application Priority Data

May 31, 2006   (DE) .......................... 10 2006 025 763

(51) Int. Cl.
*H04L 9/32* (2006.01)
*H04L 29/06* (2006.01)
*G06Q 10/00* (2012.01)
*G06Q 50/00* (2012.01)

(52) U.S. Cl.
USPC ........... 713/171; 713/150; 713/168; 713/172; 705/2; 705/3

(58) Field of Classification Search
USPC .................... 713/150, 168, 171; 705/1.1, 2, 3
See application file for complete search history.

(56) References Cited

U.S. PATENT DOCUMENTS

| 6,259,909 | B1 | 7/2001 | Ratayczak et al. |
| 6,463,417 | B1 | 10/2002 | Schoenberg |
| 6,920,559 | B1 | 7/2005 | Chen |
| 2002/0029157 | A1 | 3/2002 | Marchosky |
| 2003/0074564 | A1 | 4/2003 | Peterson |
| 2004/0088551 | A1 | 5/2004 | Dor |
| 2005/0153741 | A1* | 7/2005 | Chen et al. ..................... 455/558 |
| 2006/0080525 | A1 | 4/2006 | Ritter |

FOREIGN PATENT DOCUMENTS

| JP | 2002288341 A | 10/2002 |
| JP | 200300572 A | 1/2003 |
| JP | 2003524269 A | 8/2003 |
| WO | WO 2004052026 A2 | 6/2004 |
| WO | WO 2004104898 A2 | 12/2004 |

OTHER PUBLICATIONS

Japanese office action dated Jun. 28, 2012 (dispatched on Jul. 3, 2012) and Eng translation.

* cited by examiner

*Primary Examiner* — Taghi Arani
*Assistant Examiner* — Jahangir Kabir
(74) *Attorney, Agent, or Firm* — Schiff Hardin LLP

(57) ABSTRACT

A method for identifying a patient for later access to an electronic patient record for the patient using a communication device belonging to an inquiring person. The patient record is stored in a database using a primary key which serves to identify the patient and which has at least one unambiguously associated secondary key, where the secondary key used to identify a patient is at least one subscriber information item which characterizes a subscriber in a wireless communication network. The secondary key for identification is transmitted between a mobile terminal used for communication in the wireless communication network and a portal via the at least one communication network.

3 Claims, 3 Drawing Sheets

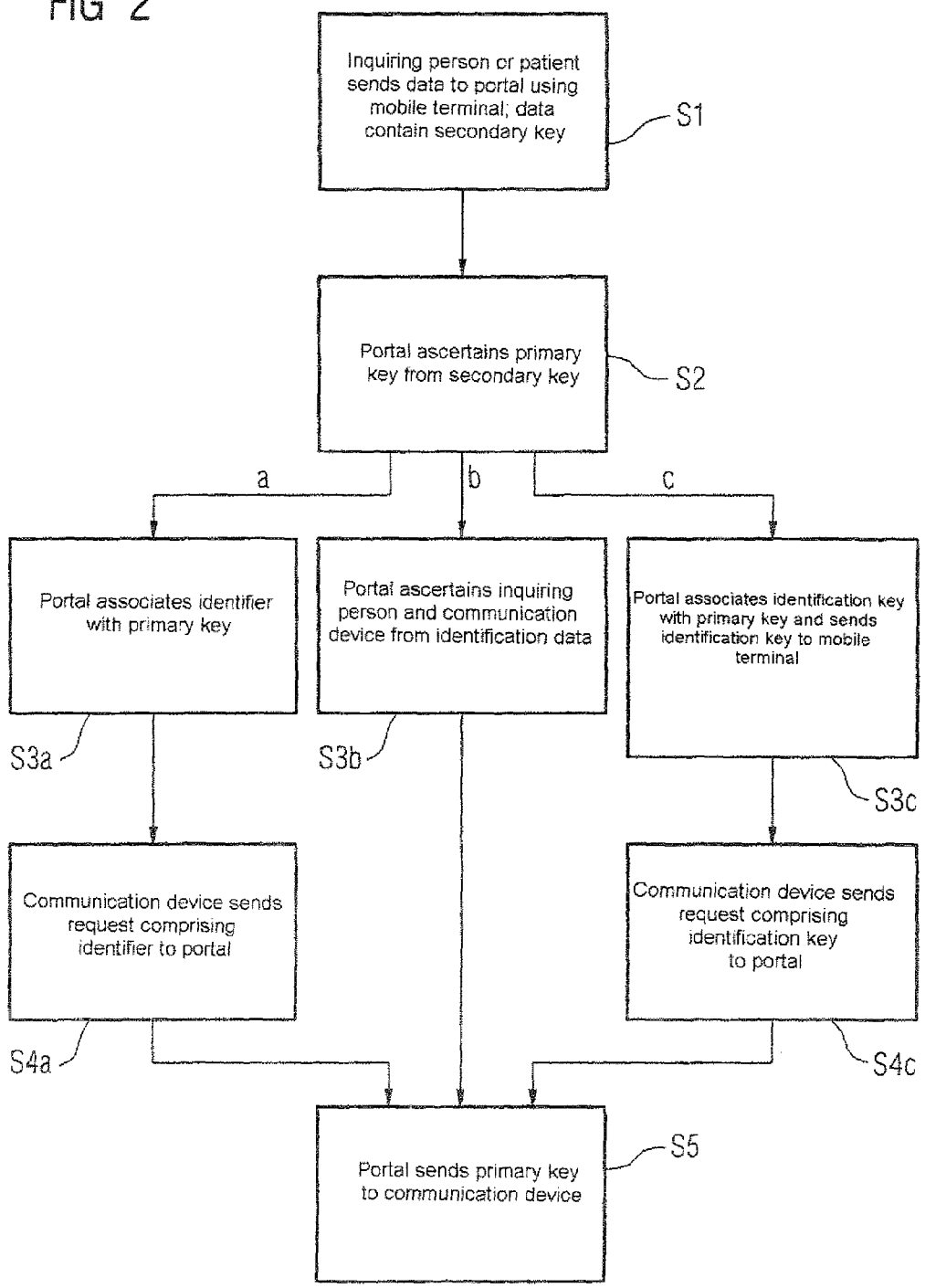

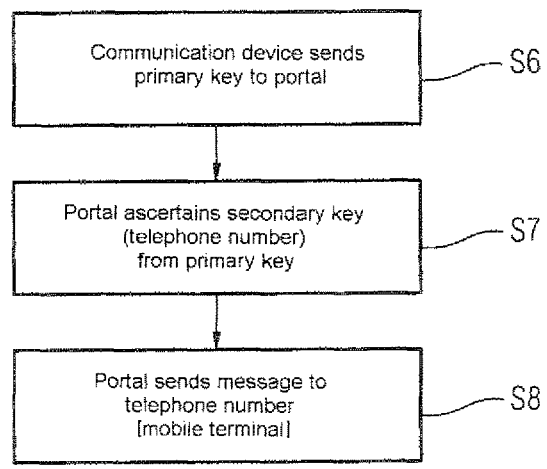
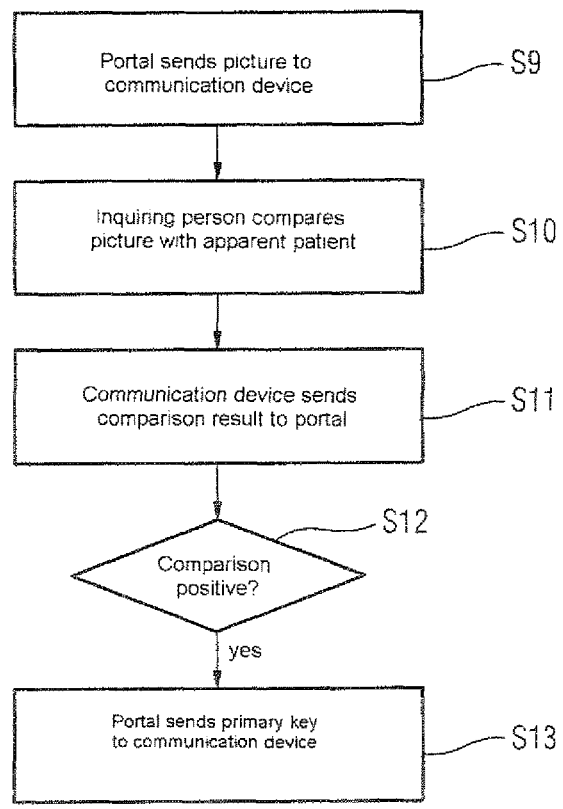

METHOD FOR IDENTIFYING A PATIENT FOR LATER ACCESS TO AN ELECTRONIC PATIENT RECORD FOR THE PATIENT USING A COMMUNICATION DEVICE BELONGING TO AN INQUIRING PERSON

BACKGROUND OF THE INVENTION

1. Field of the Invention

The present invention relates generally to a method for identifying a patient for later access to an electronic patient record for the patient using a communication device belonging to an inquiring person, the patient record being stored in a database using a primary key which serves to identify the patient and which has at least one unambiguously associated secondary key.

2. Description of the Related Art

For comprehensive, high-quality care for a patient in a health system, it is advantageous if the patient's data are stored in an electronic patient record which can ideally be accessed from anywhere in the world. By way of example, such patient records then contain not only the relevant patient's medical history but also pictures or test results.

In this case, the individual electronic patient records correspond to entries in a database which distinguishes between the individual patient records internally using a primary key. Each patient record therefore has an unambiguously associated primary key. However, the primary keys are allocated automatically and have no specific relationship with the patient him or herself. The primary key thus allows a patient record for a specific patient to be found, but does not characterize the patient himself. It has therefore been proposed that secondary keys be used which have a specific relationship with the patient as a person. The use of names and dates of birth is generally found to be not ideally suited, however, on account of these not being unambiguous and specific to one person.

It has been proposed that a health insurance card, for example, be used as a storage medium for the primary key or a secondary key. Reading such a health insurance card requires additional devices which may not be available, for example, to an emergency doctor or emergency medical technician, since the emergency medical personnel would need to constantly carry such reading device in order to identify a patient without any doubt, that is to say to find out the primary key for the patient's electronic patient record. Particularly in emergencies, it is important to identify the patient quickly and reliably, since the use of incorrect health data by a health professional can easily lead to complications.

SUMMARY OF THE INVENTION

The present invention therefore provides a method for identifying a patient, wherein the identify of the patient includes finding a patient's primary key, which allows the identity of a patient to be established with as little doubt as possible without complex, additional hardware.

To achieve this, the present invention provides a method for identifying a patient for later access to an electronic patient record for the patient using a communication device belonging to an inquiring person, the patient record being stored in a database using a primary key which serves to identify the patient and which has at least one unambiguously associated secondary key, wherein the secondary key used to identify a patient is at least one subscriber information item which characterizes a subscriber in a wireless communication network. The secondary key for identification is transmitted between a mobile terminal (such as a mobile telephone or other mobile communication device) used for communication in the wireless communication network and a portal via the and/or at least one communication network.

BRIEF DESCRIPTION OF THE DRAWINGS

FIG. 2 is a first flowchart of a method according to the principles of the present invention, FIG. 3 is a second flowchart of the present method; and FIG. 4 is a flowchart of the identity verification based on the inventive method.

DETAILED DESCRIPTION OF THE PREFERRED EMBODIMENTS

Figure 1:
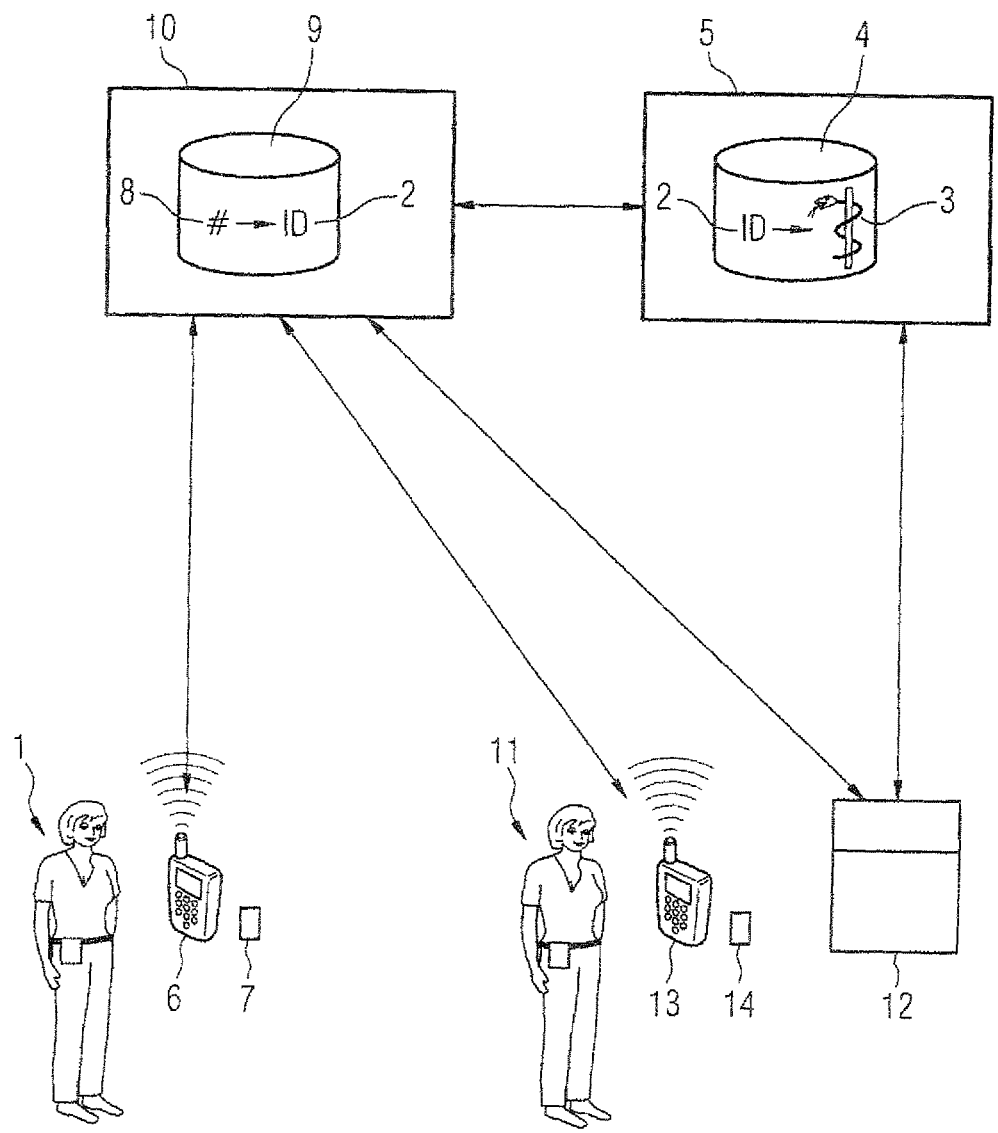
FIG. 1 is a functional block diagram showing components of a system in which the inventive method is applied.

The present invention provides that a secondary key is used to identify a patient, the secondary key being information which characterizes a subscriber in a wireless communication network. Such a subscriber information item may be, by way of example, a number from a SIM (Subscriber Identity Module) card and/or a telephone number for the patient and/or a device number for a mobile terminal (such as a mobile telephone or other mobile communication device) belonging to the patient which is used for communication in the wireless communication network. A mobile terminal within the meaning of the invention is a mobile telephone, for example, but also any other mobile device which is suitable for wireless communication in the wireless communication network, for example network-compatible PDAs (Personal Digital Assistant), mobile electronic mail device or other mobile communications device.

In accordance with the principles of the present invention, the mobile terminal thus advantageously involves the use of devices which many patients carry with them at all times anyway. To use the wireless communication network, it is necessary to have the mobile terminal and a SIM card which plugs into it. In this context, each mobile terminal has its own, unambiguous device number which distinguishes it from all other mobile terminals, for example what is known as the IMEI (International Mobile Equipment Identity) number. The IMEI is an unambiguous, 15-digit serial number which can be used to unambiguously identify any GSM (Global System for Mobile communication) or UMTS (Universal Mobile Telecommunications System) terminal. A SIM card also has an unambiguous SIM card number, which provides the mobile terminal with the patient's telephone number—which is likewise unambiguous. This has already mentioned three examples of subscriber information which is characteristic of any subscriber on the wireless communication network and which this subscriber typically carries with them. The idea on which the invention is based is to use this subscriber information which unambiguously identifies the patient and which is available anyway, as a secondary key which is unambiguously associated with the primary key. In this context, it is also possible for several such subscriber information items to be unambiguously associated with the primary key as a secondary key. In one example, all such subscriber information items are used as a secondary key associated with the primary key.

Advantageously, it is then also possible to use the relevant associated hardware, that is to say the mobile terminal, in order to establish the actual identity, that is to say the primary key, of the patient. To this end, communication takes place with a portal which stores the association between the respective secondary keys and the primary keys. This may in the first instance be the device which also stores the database with the electronic patient records, the secondary keys also being stored in this database. However, it is also conceivable for a second database that is stored on the portal to be used, which contains the secondary key(s) in association with the primary key. The database containing the electronic patient records may then be stored on another device. Something of this kind is found to be advantageous, in particular, when the cooperation with an operator of such a wireless communication network is sought, but the operator is itself not intended to be provided with any kind of access to the electronic patient records, for example for reasons of data protection. There are then two databases, therefore, and a secondary key can be associated with a primary key without any difficulty in the second database stored on the portal.

The communication device of the inquiring person may be any type of communication device which is designed to access the electronic patient record. A special communication device for accessing the patient record may be provided, but it is also possible to design known communication devices such as workstation computer, laptops, handhelds or even mobile telephones, for example using a software means, such that access to electronic patient records in the database becomes possible.

To identify the patient, which here refers to finding the primary key which makes it possible to find the patient's record, the invention provides for communication with the portal and a mobile terminal. In this case the secondary key is transmitted, which can be associated with a primary key or vice versa without any difficulty. By way of example, the primary key can then be transmitted to the communication device of an inquiring person. By way of example, an inquiring person of this kind may be a health professional, for example a doctor, a paramedic, or the like. For the specific refinement of the transmission and the resultant identification of a patient, various refinements are conceivable in line with the principles of the invention.

Thus, a provision may be made for the patient to be identified using a mobile terminal belonging to the patient or a mobile terminal which is provided with a SIM card belonging to the patient and which sends data to the portal and/or receives data from the portal. In this context, the identification is made using data which are sent from the mobile terminal to the portal or from the portal to the mobile terminal. In this case, it is important for the mobile terminal of the patient (specifically, the mobile terminal device number) or the SIM card of the patient (specifically, the SIM card number and/or telephone number) or both to be used, so that at least one of the secondary keys can be transmitted or can be checked.

In a further refinement of the invention, a provision may be made for the mobile terminal to send data comprising the secondary key(s), particularly in the form of an SMS (Short Message Service) message or by means of GPRS (General Packet Radio Service), to the portal, for the portal to take the secondary key(s) as a basis for ascertaining the primary key, and for further information which the data comprise to be used to transmit the primary key to the communication device. This includes the cases of forward identification, for example. With forward identification, the patient himself or herself initiates the authentication in the broader sense, in this case by sending an SMS or a GPRS data packet to the portal, for example. In this context, the data comprises one or more secondary keys, the telephone number itself being automatically contained in the data in the case of an SMS, for example. In addition to the secondary keys, the data contain further information, however, which either allows the inquiring person to find the patient's primary key without any doubt or even allows the portal to identify the inquiring person and in this case to transmit the primary key, so that the patient is ultimately identified. For the further information, several advantageous options are suitable in this case.

Thus, provision may be made for the data to comprise an unambiguous identifier, which identifier is sent from the communication device to the portal, which transmits the primary key to the communication device in response. An unambiguous identifier of this kind may be what is known as a "challenge", for example. By way of example, a random number which is unambiguous throughout the system is generated which is transmitted to the portal. The portal uses the secondary key(s) to ascertain the primary key which is associated with the respective patient and assigns the respective patient, possibly only temporarily in order to prevent misuse, this random number, which is generally the unambiguous identifier. The communication device can then be used to send the same random number or the identifier as a request to the portal. The communication device thus inquires as to who recently transmitted the relevant random number or unambiguous identifier to the portal. The portal, which has stored the identifier in association with the primary key, can now send the primary key to the inquiring communication device. The unambiguous identifier can be transmitted from the mobile terminal to the communication device in various conceivable ways, for example informally, by virtue of the patient notifying the inquiring person of it.

In this case, it is of no consequence whether or not it is possible to talk to the patient. By way of example, provision may be made for a prescribed SMS or a software means to be provided on the mobile terminal for emergency situations, the mobile terminal easily producing relevant data comprising the identifier and the secondary key and transmitting them to the portal. It is thus also possible to identify a patient to whom it is not possible to talk whose mobile terminal or SIM card is fully operational.

As an alternative to the unambiguous identifier, it is conceivable to use GPS (Global Positioning Satellite) coordinates. This requires both the mobile terminal and the communication device to be equipped with a GPS sensor and to be at the same location, he secondary key(s) can then be transmitted to the portal as data together with the GPS coordinates as an unambiguous identifier, on the basis of which the communication device can identify itself without further data interchange, since it is at the same location, using GPS coordinates which can be sent at the push of a button, for example, and receives the primary key. This is very advantageous particularly in emergency situations in which rapid access to the electronic patient record and therefore rapid identification of the patient is desired, since there is no need for any informal or other kind of interchange of the identifier to take place between the mobile terminal and the communication device.

In another embodiment, the data comprise identification data from the inquiring person which the portal uses to ascertain the communication device and to transmit the primary key to the communication device. Accordingly, the inquiring person has a communication device which is personalized for him or her and the data contain identification data for identifying the inquiring person. By way of example, these identification data may be a number for identifying a doctor or other health professional. In this case, each inquiring person has a personalized communication device which can be associated with him or her. By way of example, this may be a doctors desktop PC or else a device which a paramedic carries with them in order to access patient records when the medical personnel is on the go.

It is particularly advantageous if the inquiring person himself is recorded in the database(s) and therefore also has an associated secondary key which is a subscriber information item characterizing a subscriber in a wireless communication network. Under these circumstances particularly for emergencies, two refinements of the method are conceivable which allow the identification data and the secondary key(s) relating to the patient to be transmitted as data to the portal without any further, possibly time-consuming, inputs. Thus, provision may be made for the patient's SIM card to be used in a mobile terminal belonging to the inquiring person, and for the SIM-card-related secondary key to be used to ascertain the primary key, and for the mobile terminal device number to be used, possibly as a secondary key, to ascertain the inquiring person and hence the communication device. If the patient's mobile terminal is unavailable or is faulty then the doctor can use the doctor's mobile terminal for the request. Several refinements are conceivable in this context. If it is possible to talk to the patient then the patient can communicate his or her PIN (Personal Identification Number) to the inquiring person in order to activate the SIM card in the mobile terminal of the inquiring person. In one alternative, provision may be made—through appropriate adaptation of the data structure on the SIM card or through appropriate design of the mobile terminal—for there to be not only the input request for inputting the PIN but additionally an emergency option whose activation sends a predefined SMS, a GPRS packet or the like, which comprises the identification data and the secondary keys of the patient, to the portal, for example. In a third refinement, it is likewise conceivable for the inquiring person's mobile terminal to have a plurality of slots for SIM cards and for the patient's SIM card to be able to be read after being inserted into one of the additional slots in order to obtain the secondary key(s).

As an alternative to this, provision may also be made for the inquiring person's SIM card to be used in a mobile terminal belonging to the patient, and for a SIM-card-related information item to be used, possibly as secondary key, to ascertain the inquiring person and hence the communication device, and for the mobile terminal device number to be used as a secondary key to ascertain the primary key. This embodiment, in contrast to the previous one, requires no communication between the patient and the inquiring person and no modification of the mobile terminal, but rather, if the patients mobile terminal is operational, the mobile terminal can be used regardless of its state, since the SIM card of the inquiring person, for example the health professional, is used. By way of example, the inquiring person then sends a predefined SMS (Short Message Service) signal, which also contains the IMEI (International Mobile Equipment Identity) number of the mobile terminal, to the portal and thus identifies the health professional and the patient, so that the health professional receives the latter's primary key on his or her communication device.

As already mentioned, the refinements in which identification data from the inquiring person are also sent are expedient particularly when the inquiring person can be identified by an appropriate secondary key in the database system. In the cases cited, it is then necessary to use a plurality of secondary keys in all cases, however, for example the mobile terminal device number and the telephone number and/or the SIM card number.

In a further expedient refinement, however, the data can also be in the form of an access request. In this case, the patient or the inquiring person can send an access request comprising the secondary key(s) from the mobile terminal to the portal, the portal then transmits an identification key associated with the primary key ascertained using the secondary key(s) to the mobile communication terminal, which identification key is sent to the portal via the communication device, and then the portal transmits the primary key to the communication device. In this context, a somewhat more reliable variant is proposed, where—for example again as a result of an appropriate option on the mobile terminal—an SMS comprising at least the secondary key(s) is sent to the portal. Alternatively, GPRS (General Packet Radio Service), WAP (Wireless Application Protocol) or similar transmission options are naturally conceivable in this case too. Instead of transmitting the primary key on a direct path, however, the portal now associates an identification key with the primary key, the identification key being returned to the same mobile terminal from which the request was made. This identification key then corresponds in principle to a kind of identification code which can be used only with a communication device of appropriate design. It may thus be in the form of a kind of access code.

In a further embodiment, an identification key with a limited validity period can be used. By way of example, this also allows access to the patient's electronic patient record at restricted times which can be replated. In addition, a risk of misuse is reduced. When it is possible for the patient to talk, the patient can request the identification key, for example for a health professional treating him, and can pass it on to the health professional. Only a health professional with a communication device can then use it. However, the same applies when it is not possible to talk to the patient, and, by way of example, a health professional or another inquiring person wishes to ascertain an identification key in an emergency.

The possibilities mentioned in the foregoing correspond to forward identification. In this case, it is necessary to know, not even through supposition, who the patient is, that is to say which primary key is associated with the patient. However, what is known as backward identification is also possible within the context of the inventive method. In the case of backward identification, it is supposed, for example on the basis of the name and the date of birth of the patient, who the patient might be, that is to say which primary key is associated with the patient. This supposed identity should then be checked for reliably identifying the patient.

In this regard, a provision may expediently be made for the inquiring person to use the communication device to send data comprising a supposed primary key for the patient to the portal, and then for the portal to send a message, particularly an SMS signal, to a telephone number, used as a secondary key, for a patient ascertained using the primary key. Alternatively, it is also conceivable for the portal to make a call to the patient, in particular automatically. In this case, the content of such a message may be in any form. The inquiring person ultimately asks the patient or takes an appropriate look at the patient's mobile terminal or the mobile terminal containing the patient's SIM card to establish whether the primary key which the health professional has found is the correct primary key. In this case, the method thus provides a method of reassurance which allows mix ups to be practically ruled out. If the patient does not receive such a message or such a call then it is known that the primary key is obviously not correct.

The secondary key does not necessarily need to be transmitted via the wireless communication network to which the subscriber information refers in order to find the primary key, however. In another refinement of the method, it is also conceivable for the secondary key(s) to be transmitted between the mobile terminal and the communication device via a wireless communication link, particularly via an infrared link or Bluetooth link, and then for the communication device to send the secondary key to the portal, and for the portal to ascertain the primary key from the secondary key and to transmit it to the communication device. This in turn requires an appropriate design for the mobile terminal, which can be implemented by providing an appropriate software means. A patient then initiates the relevant function on his mobile terminal, and then an appropriate link, for example a Bluetooth link or infrared link, is set up which is used to transmit the secondary key(s). If the inquiring person's secondary key(s) are first of all known and available on the communication device, they can be sent to the portal, which ascertains the associated primary key and transmits it back to the communication device, so that the inquiring person finds out the relevant identity of the patient and, if appropriate, can access his electronic patient record.

At this juncture, it should be noted that, by way of example, to implement the relevant data protection provisions, further safety precautions can be taken for actually accessing the respective electronic patient record. If appropriate, just finding out the primary key needs to be classified as critical, however. In any case, the inclusion of the patient in the system may involve an authorization being provided which the patient uses to authorize people or groups of people, possibly when particular circumstances arise, to access information, particularly the primary key and the electronic patient record itself. In the case of forward identification when it is possible to talk to patients addressed, it is possible to achieve case-by-case release of the primary key/the electronic patient record by means of the combination, permitted by the method, of the identity of the inquiring person, particularly of the health professional, preferably likewise using the secondary key(s), with a specifically provided PTN, signature or similar code for the patient. However, for emergencies, for example, it is particularly expedient if the electronic patient record or the primary key is on general release, which has been stored in advance, in the form of an authorization, this authorization being provided only for particular inquiring people, particularly health professionals, who need to act quickly in emergencies, however. The identity of the health professional or the use of the relevant communication device can then grant the health professional the appropriate access.

The instances discussed in the forgoing deal essentially with a patient to whom it is possible to talk or who has an operational mobile terminal or a SIM card which is suitable for initiating an appropriate emergency transmission even when it has been inserted into a mobile terminal belonging to another person. However, it is also conceivable for an emergency key to be stored on the SIM card. This emergency key that is stored on the patient's SIM card can then be read by the inquiring person's communication device and transmitted to the portal, and then the portal can use the emergency key used as secondary key to ascertain the patient's primary key and to transmit it to the communication device. The primary key can then be ascertained in all cases and hence the patient identified.

If, furthermore, the patient's SIM card is also faulty or damaged, the SIM card number is usually also printed on the SIM card itself, so that this secondary key can still be ascertained. A similar situation may also apply to the IMEI number.

Since mobile terminals and SIM cards may also, in some cases involuntarily, change possession, such as by being borrowed or stolen, without this being indicated, it is particularly advantageous if a further check on the identity of a patient can take place. By way of example, this can be achieved by virtue of the invention providing for further identity verification to take place on the basis of biometric features and/or a picture of the patient, these being interchanged between the portal and the mobile terminal and/or the communication device. In this context, a check is accordingly performed to determine whether the actual patient is associated with the mobile terminal found on the patient or with the SIM card found on the patient.

More specifically, provision may be made in this context for the mobile terminal and/or the communication device to be equipped with a biometric sensor system and/or a camera. A picture or biometric data from the patient can then be sent to the portal and compared with biometric data stored there, particularly in the second database, or with a picture stored there, and the result of the comparison can be transmitted to the mobile terminal and/or to the communication device. The patient's identity ascertained by the secondary key(s) is thus additionally checked either using biometric features, for example a fingerprint or a retinal scan, or else a picture, which are respectively compared by the database with previously stored biometric data or a picture. The result of this comparison is returned to the device which sent the biometric data used for the check or the picture used for the check. This prevents incorrect health data from an electronic patient record which is not at all associated with the patient and which has been obtained as a result, for example when a mobile phone has been borrowed, from being used with possibly even critical consequences.

As an alternative to equipping the mobile terminal or the communication device with a camera or appropriate biometric sensors, a provision may also be made for a picture of the associated patient, which has been stored beforehand in the (second) database, to be sent to the communication device upon or before transmission of a primary key. In this case, the inquiring person also receives a picture of the patient, which he is able to compare with the appearance of the person to be identified. This allows particularly simple identity verification and further reduces incorrect associations between primary keys and patients. In particular, provision may be made for initially only sending the picture of the patient to the communication device. In this case, the primary key is not transmitted until after a confirmed comparison of the picture with a person who appears to be the patient has been made. For this, an appropriate confirmation is then sent from the communication device to the portal and then the primary key is sent to the communication device. In this case, the identity verification is provided as an unambiguous step in the identification process which needs to be completed first before the primary key is made available to the inquiring person.

The inventive method thus uses already existing infrastructures and a personalization (personal identification) stage which is available anyway, namely the subscriber information, to afford a way of identifying a patient, that is to say of finding a primary key for which further devices or personalization stages are no longer necessary. In particular, the basic idea of the invention can be advantageously extended in this direction. Thus, by way of example, the patient's SIM card may also replace an existing health insurance card which have been used in the past, since the SIM card is also personalized for the relevant patient and unambiguously identifies the patient. By linking secondary keys relating to the SIM card to the primary key from the electronic patient record, it is then possible, even without an electronic health insurance card, to associate the patient with a patient record and hence also with a health insurance company. In addition, the storage possibilities on a SIM card can also be used for such information.

In another development of the inventive idea, it is also conceivable for it to be possible to bill for medical services via a mobile communication provider. Since the patient can be identified in the mobile communication provider's wireless communication network, and is also accordingly handled via the portal, which, of course, may be arranged in the mobile communication provider's area of coverage, for example, it is also conceivable to bill for the medical services by this means, which dispenses with a certain amount of management complexity.

The inventive method will now be explained in more detail with reference to the drawings show shows a few exemplary embodiments. First of all, FIG. 1 shows important components of a system in which the inventive method is performed. In this case, the arrows between the components indicate possible communication paths; it should be noted, however, that not every one of the communication paths indicated is used in every direction in each of the embodiments.

The inventive method is intended to identify a patient 1, that is to say it is intended for the primary key 2 to be found, which characterizes an electronic patient record 3 with health data for the patient in a first database 4, which is stored on a server 5, for example. The patient 1 is a subscriber in a wireless communication network. For communication in this network, the patient has a mobile terminal 6, in this case a mobile telephone, which has a mobile terminal device number which is unambiguous, particularly an IMEI. In addition, the patient 1 has a SIM card 7 which has a likewise unambiguous SIM card number and assigns the patient 1 an unambiguous telephone number. The mobile terminal device number, the telephone number and the SIM card number provide a personalization stage for the patient 1 which allows the patient 1 to be unambiguously identified. For that reason, one or more of these subscriber information items are used as a secondary key 8 which is unambiguously associated with the relevant primary key 2 in a second database 9. The second database 9 is stored in a portal 10. However, it is also possible for the first database 4 and the second database 9 to be implemented as a single database which can then also be stored in the portal or a server communicating with the portal. In the present case, the portal 10 is associated with the sphere of influence of a mobile communication provider, whereas the electronic patient records are managed on a further server 5 which is external to this.

An inquiring person 11, particularly a health professional, wishes to unambiguously identify the patient 1, that is to say to find out the patient's primary key 2, so as later to be able to use a communication device 12 designed for this purpose to access the electronic patient record 3. The inquiring person 11 may also have a mobile terminal 13 and a SIM card 14, which represent an appropriate personalization stage for the health professional.

In this context, it should be noted that the communication device 12 itself may also be a mobile terminal, that is to say that the communication device 12 and the mobile terminal 13 do not need to be separate units.

FIG. 2 shows a first flowchart in which embodiments of the method for forward identification are explained in more detail.

First of all, data are sent to the portal 10 using the mobile terminal 6 or 13 in step S1. These data contain at least one secondary key 8 for the patient 1. Who initiates transmission of the data is essentially dependent on whether it is possible to talk to the patient 1. The transmission of the data can be initiated either by the patient 1 or by the inquiring person 11.

The data can be sent in different ways, for example in the form of an SMS message, using GPRS (General Packet Radio Service) or WAP (Wireless Application Protocol) or using other transmission techniques. What is relevant is that at least one secondary key 8 for the patient 1 is contained therein. A telephone number is sent anyway when the SIM card 7 of the patient 1 is used, and other secondary keys can be ascertained and added to the data using a suitable software means, for example. A preworded SMS signal may also be provided. Overall, a large number of refinement options are conceivable.

The data are sent by a mobile terminal, that is to say by the mobile terminal 6 of the patient 1, by the mobile terminal 13 of the inquiring person 11 or by another mobile terminal. Since at least one secondary key 8 from the patient 1 is required, the following configurations are conceivable and reasonable. First, it is naturally possible to use the patient's mobile terminal 6 with the patient's SIM card 7. However, it is also possible to use the patient's mobile terminal 6 with the SIM card 14 of the inquiring person 11 or with another SIM card. Equally, the mobile terminal 13 belonging to the inquiring person 11 or another mobile terminal may be used with the SIM card 7 of the patient 1. In all of these cases, at least one of the secondary keys is available.

In all instances referring to use of the mobile telephone or terminal of the health professional, it is also within the scope of the present invention that the mobile terminal could belong to a third party, such as a bystander or assistant, or to the employer of the health professional or to another entity. The mobile terminal may be a mobile telephone, mobile electronic mail device, mobile internet device, mobile gaming device, personal digital assistant, or other wireless portable device.

In step S2, the data are received by the portal 10, which ascertains the primary key 2 from the secondary key 8, which is contained in the data, of course, in the database 9.

As the method continues, several refinements of forward identification are conceivable which are identified by a, b and c in FIG. 2.

In case a, the data sent to the portal 10 additionally comprise an unambiguous identifier for the portal 10. This may be an unambiguous random number, for example within the context of what is known as a "challenge". However, it is also possible to use GPS coordinates for the relevant mobile terminal 6 or 13, possibly with a time frame or time stamp. When the primary key 2 has been ascertained from the secondary key 8, the portal 10 associates the identifier likewise contained in the data with the primary key 2 in step S3a. The inquiring person 11 can then use the communication device 12 to send a request comprising the identifier to the portal 10. This is done in step S4a. On the basis of the identifier, the portal 10 can ascertain the primary key 2 and can send it to the communication device 12 in step S5. It goes without saying that in this case the portal 10 also knows the origin of the request, which means that this identifies the communication device 12 and it is possible for the primary key 2 to be sent to it.

In the alternative embodiment b, the data sent to the portal 10 comprise identification data which are used to identify the inquiring person 11 and hence the communication device 12 personally associated with him. It goes without saying that it is also possible to send identification data at the same time, which are used directly for identifying the communication device 12. In step S3b, the portal 10 uses these identification data to ascertain the inquiring person 11 and/or the communication device 12. In this context, it is particularly advantageous if the inquiring person 12 is also present in the database system, so that in this case too secondary keys are associated which characterize the inquiring person 11 as a subscriber in the wireless communication network. Particularly in that case, two simple, alternative methods are conceivable for simultaneously identifying the patient 1 and the inquiring person 11 and hence the communication device 12. First, it is possible for the SIM card 14 of the inquiring person 11 to have been inserted into the mobile terminal 6 of the patient 1. Using the secondary key(s), SIM card number and/or telephone number, it is possible to identify the inquiring person 11, and using the mobile terminal device number for the mobile terminal 6 as secondary key, it is possible to ascertain the patient 1. It is naturally also possible for the SIM card 7 of the patient 1 to be inserted into the mobile terminal 13 of the inquiring person 11. It is then possible for the inquiring person 11 to be ascertained using the mobile terminal device number of the mobile terminal 13 and for the patient 1 to be ascertained using the SIM card number of the SIM card 7 and/or the telephone number. It goes without saying that it is also conceivable for the identification data sent to be a special health professional identifier, for example a code number which the inquiring person 11 uses to identify himself to the portal 10.

Once the inquiring person 11 and hence the communication device 12 have been identified, the portal 10 again transmits the primary key 2 of the patient 1 to the communication device 12 in step S5.

In a further variant, variant c, only the secondary key 8 is transmitted in the data. In step S3c, the portal 10 then associates an unambiguous, generated identification key with the primary key 2, which identification key is returned to the respective mobile terminal 6 or 13. If the patient 1 is the person making the inquiry, the identification key can be transmitted to the inquiring person 11 and hence to the communication device 12 as part of an informal interchange. If the user of the inquiring mobile terminal 6 or 13 is the inquiring person 11 himself, he is provided with knowledge of the identification key directly. This identification key may have a limited validity period, for example, in order to avoid misuse.

In step S4c, the communication device 12 then sends a request comprising the identification key to the portal 10, he portal 10 can use the identification key to ascertain the primary key 2 of the patient 1 in turn, and again sends it to the communication device 12 in step S5.

The inventive method can also be used for backward identification, however. This is shown in more detail in a second flowchart in FIG. 3. Backward identification means that the inquiring person 11 already supposes a primary key 2 for the patient 1 and wishes to have this primary key 2 confirmed. To this end, in step S6 the communication device 12 sends the primary key within a request to the portal 10. In step S7, the portal 10 ascertains the secondary key 8, particularly the telephone number, from the primary key 2. Since the telephone number of the patient 1 is now known, the portal 10 can send a message to this telephone number in step S8 which then reaches the mobile terminal which contains the SIM card 7 of the patient 1, that is to say usually the mobile terminal 6. The patient 1 or the inquiring person 11 can then check, following receipt of the message, whether the primary key 2 is actually associated with the patient 1.

Finally, FIG. 4 shows a possibility for further identity verification in the inventive method. Steps S9 to S13 shown in FIG. 4 are carried out before step S5 in FIG. 2, for example. In this case, the portal 10 does not immediately send the primary key 2 to the communication device 12, but first of all sends a picture of the patient 1 which has previously been stored in the portal 10, particularly in the second database 9, to the communication device 12. This is done in step S9. The inquiring person 11 can then compare the picture with the apparent patient 1 in order to establish whether the person is actually the patient 1, when this has been done in step S11, the communication device 12 sends the comparison result back to the portal 10 in step S11, and then in step S12 the portal 10 checks whether the outcome of the comparison was positive or negative. If the outcome of the comparison was negative, the primary key 2 is not associated with the person which the inquiring person 11 took to be the patient 1. No further measures are then necessary. If the identity of the patient 1 is confirmed, however, the portal sends the primary key 2 to the communication device 12 in step S13.

Thus, there is shown and described a method for identifying a patient for later access to an electronic patient record for the patient using a communication device belonging to an inquiring person, which patient record is stored in a database using a primary key which serves to identify the patient and which has at least one unambiguously associated secondary key, where the secondary key used to identify a patient is at least one subscriber information item which characterizes a subscriber in a wireless communication network, which secondary key for identification is transmitted between a mobile terminal used for communication in the wireless communication network and a portal via the or at least one communication network.

Although other modifications and changes may be suggested by those skilled in the art, it is the intention of the inventors to embody within the patent warranted hereon all changes and modifications as reasonably and properly come within the scope of their contribution to the art.

We claim:

1. A method for identifying a patient for later access to an electronic patient record for the patient using a mobile terminal belonging to an inquiring person, comprising:

storing the electronic patient record in a database of patient records using primary keys to identify patient records of patients within the database, each of the primary keys identifying only one patient record;

unambiguously associating a secondary key with one of the primary keys, the secondary key identifying only one primary key, the secondary key being a number associated with a telephone of the patient including at least one of a telephone number of the patient's telephone, a Subscriber Identity Module (SIM) card number of the SIM card of the patient's telephone, and an International Mobile Equipment Identity (IMEI) number of the patient's telephone, wherein the patient's telephone is used by the patient as a subscriber in a wireless communication network, the secondary key being unambiguously associated with the patient;

using the secondary key used to identify a patient, including:

transmitting the secondary key from a mobile terminal used for communication in the wireless communication network to a portal via at least one communication network, the portal providing communication to a stored association between the secondary key and the primary key; and identifying the primary key of the patient record for the patient using the transmitted secondary key to locate the stored association of the secondary key and the primary key of the patient;

requiring identification of the inquiring person as an authorized person for access to the patient records of the patient; and granting to an authorized person access to the patient records of the patient.

2. A method as claimed in claim 1, further comprising the step of:

using the identified primary key to access the patient records of the patient.

3. A method for identifying a patient for later access to an electronic patient record for the patient using a mobile terminal belonging to an inquiring person, comprising:
- storing the electronic patient record of the patient in a database of patient records;
- automatically allocating a primary key to identify the patient record of the patient within the database, the primary key identifying only one patient record within the database;
- receiving a secondary key of the patient, the secondary key being a number associated with a telephone of the patient including at least one of a telephone number of the patient's telephone, a Subscriber Identity Module (SIM) card number of the SIM card of the patient's telephone, and an International Mobile Equipment Identity (IMEI) number of the patient's telephone, wherein the patient's telephone is used by the patient as a subscriber in a wireless communication network, the patient being a subscriber in the wireless communication network;
- unambiguously associating the secondary key of the patient with the primary key allocated to the patient records of the patient, the secondary key identifying only one primary key, the association between the primary key and the secondary key being provided by a database stored at a portal;
- using the secondary key used to identify the patient, including:
  - transmitting the secondary key from a mobile terminal used for communication in the wireless communication network to the portal via at least one communication network, the portal providing communication to the database in which is stored the association between the secondary key and the primary key;
  - identifying the primary key of the patient record for the patient using the transmitted secondary key to locate the stored association of the secondary key and the primary key of the patient in the database; and
  - retrieving patient information from the electronic patient record for the patient using the identified primary key;
- requiring identification of the inquiring person as an authorized person for access to the patient records of the patient; and
- granting to an authorized person access to the patient records of the patient.

* * * * *